United States Patent [19]
Djuric et al.

[11] Patent Number: 5,578,619
[45] Date of Patent: Nov. 26, 1996

[54] ALKOXY-SUBSTITUTED DIHYDROBENZOPYRAN-2-SULFONIMIDES

[76] Inventors: Stevan W. Djuric, 924 Dolphin Dr., Malvern, Pa. 19355; Thomas D. Penning, 374 Larch, Elmhurst, Ill. 60126

[21] Appl. No.: 569,323

[22] Filed: Dec. 8, 1995

Related U.S. Application Data

[63] Continuation of Ser. No. 249,107, May 25, 1994, abandoned.

[51] Int. Cl.$^6$ .................... C07D 409/12; A61K 31/425
[52] U.S. Cl. .................... 514/365; 514/369; 514/370; 514/374+397 ; 548/187; 548/194; 548/204; 548/236; 548/525
[58] Field of Search .................... 514/365, 369, 514/370, 374, 397; 548/187, 194, 204, 230, 525

[56] References Cited

U.S. PATENT DOCUMENTS

| | | | |
|---|---|---|---|
| 4,778,903 | 10/1988 | Miyano | 549/467 |
| 4,889,871 | 12/1989 | Djuric | 514/456 |
| 5,073,562 | 12/1991 | Djuric | 514/365 |

OTHER PUBLICATIONS

N. Ahmadzadeh, et al. *Inflammation* 15:497–503 (1991) "Relationship Between Leukotriene $B_4$ and Immunological Parameters in Rheumatoid Synovial Fluids".

R. Barr et al. *Prostaglandins* 28:57–65 (1994) "The Analysis of Arachidonic Acid Metabolites in Normal, Uninvolved and Lesional Psoriatic Skin".

J. Drummond, et al. *Tetrahedron Letters* 29:1653–1656 (1988) "Convenient Procedure for the Preparation of Alkyl and Aryl Substituted N–(Aminoalkylacyl) Sulfonamides".

D. Fretland, et al. *Prostaglandins Leukotrienes and Essential Fatty Acids* 45:249–257 (1992) "Potential Role of Prostaglandins and Leukotrienes in Multiple Sclerosis and Experimental Allergic Encephalomyelitis".

V. Matassa, et al. *J. Med. Chem.* 33:1781–1790 "Evolution of a Series of Peptidoleukotriene Antagonists: Synthesis and Structure/Activity Relationships of 1,3,5–Substituted Indoles and Indazoles" 1990).

S. Rae, et al. *The Lancet* 2:1122–1123 (1982), "Leukotriene $B_4$, an Inflammatory Mediator in Gout".

T. Schaar, et al. *Journal of Medicinal Chemistry* 22:1340–1346 (1979), "Synthesis and Biological Activity of Carboxyl–Terminus Modified Prostaglandin Analogues".

P. Sharon, et al. *Gastroenterology,* 86:453–460 (1984), "Enhanced Synthesis of Leukotriene $B_4$ by Colonic Mucosa in Inflammatory Bowel Disease".

K. Shindo, et al. *Journal of Internal Medicine,* 228:91–96 (1990), "Measurement of leukotriene $B_4$ in arterial bllod of asthmatic patients during wheezing attacks".

*Primary Examiner*—Robert Gerstl
*Attorney, Agent, or Firm*—Fitzpatrick, Cella, Harper & Scinto

[57] ABSTRACT

This invention relates to compounds of Formula I and the stereoisomers and pharmaceutically acceptable salts thereof

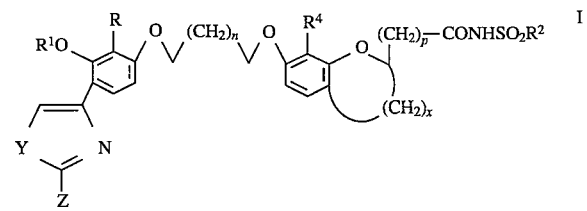

wherein R is alkyl, alkenyl, alkynyl, or $(CH_2)_m$ $R^3$ where $R^3$ is cycloalkyl and m is 1 or 2;

$R^1$ is alkyl;

$R^2$ is alkyl, aryl or aryl substituted with halogen or alkyl;

$R^4$ is alkyl;

n is an integer from 1 to 5;

p is an integer from 0 to 6;

Y is NH, oxygen or sulfur; and

Z is hydrogen, alkyl, alkoxy, $NR^6R^5$ wherein $R^6$ and $R^5$ are independently hydrogen or alkyl, or $SR^7$ wherein $R^7$ is hydrogen, benzyl or alkyl.

The compounds of Formula I are leukotriene $B_4$ antagonists and are useful as anti-inflammatory agents and in the treatment of leukotriene $B_4$ mediated conditions.

13 Claims, No Drawings

ALKOXY-SUBSTITUTED DIHYDROBENZOPYRAN-2-SULFONIMIDES

This is a Continuation of application Ser. No. 08/249,107, filed May 25, 1994 now abandoned.

BACKGROUND OF THE INVENTION

1. Field of the Invention

This invention is in the field of pharmaceutical agents which selectively act as leukotriene $B_4$ ($LTB_4$) antagonists.

2. Prior Art

Leukotriene $D_4$ and $C_4$ ($LTD_4$/$LTC_4$) and leukotriene $B_4$ ($LTB_4$) are products of the arachidonic acid metabolic pathway. $LTD_4$ and $LTC_4$ are associated with smooth muscle contraction and contract guinea pig ileum, human and guinea pig bronchi and human pulmonary artery and vein. $LTB_4$ is associated with neutrophil stimulation which is characterized by chemotaxis, aggregation and degranulation. $LTB_4$ is believed to be an important mediator of inflammation. High levels of $LTB_4$ are detected in rheumatoid arthritis, gout, psoriasis, and inflammatory bowel disease. Thus antagonists of $LTB_4$ are useful in the therapy of such diseases.

*Gastroenterology*, 1985: 88: 580–7 discusses the role of arachidonic acid metabolites in inflammatory bowel disease.

*British Medical Bulletin*, (1983), vol. 39, No. 3, pp. 249–254, generally discusses the pharmacology and pathophysiology of leukotriene $B_4$.

*Biochemical and Biophysical Research Communications*, Vol. 138, No. 2 (1986), pp. 540–546 discusses the pharmacology of a specific $LTB_4$ antagonist which has a different structure than compounds of this invention.

U.S. Pat. No. 4,889,871 discloses alkoxy-substituted dihydrobenzopyran-2-carboxylate derivatives which are selective antagonists of $LTB_4$ with little or no antagonism of $LTD_4$ and are useful as antiinflammatory agents for treating inflammatory bowel disease.

BRIEF DESCRIPTION OF THE INVENTION

This invention encompasses compounds of Formula I and the stereoisomers and pharmaceutically acceptable salts thereof;

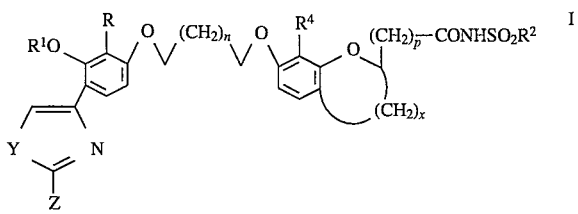

wherein

R represents alkyl having 2 to 6 carbon atoms, alkenyl having 2 to 6 carbon atoms, alkynyl having 2 to 6 carbon atoms, or $—(CH_2)_m—R^3$ wherein $R^3$ represents cycloalkyl of 3 to 5 carbons atoms and m is 1 or 2;

$R^1$ represents alkyl having 1 to 4 carbon atoms;

$R^2$ represents alkyl having 1 to 5 carbon atoms, aryl or aryl substituted with halogen or alkyl having 1 to 5 carbon atoms;

$R^4$ represents alkyl of 1 to 6 carbon atoms;

n is an integer from 1 to 5;

p is an integer from 0 to 6;

x is 0 or 2;

Y represents NH, oxygen or sulfur; and

Z represents hydrogen, alkyl having 1 to 4 carbon atoms, alkoxy having 1 to 4 carbon atoms, $NR^6R^5$ wherein $R^6$ and $R^5$ are independently hydrogen or alkyl having 1 to 4 carbon atoms, or $SR^7$ wherein $R^7$ is hydrogen, benzyl or alkyl having 1 to 4 carbon atoms.

These compounds are selective antagonists of leukotriene $B_4$ ($LTB_4$) with little or no antagonism of leukotriene $D_4$ ($LTD_4$) and are useful anti-inflammatory agents for treating inflammatory bowel disease, rheumatoid arthritis, gout, asthma, multiple sclerosis, and psoriasis and in treating conditions mediated by $LTB_4$.

DETAILED DESCRIPTION OF THE INVENTION

This invention encompasses the compounds of formula I as previously described.

Preferred embodiments of the present invention are compounds of the formula Ia, the stereoisomers and pharmaceutically acceptable salts thereof,

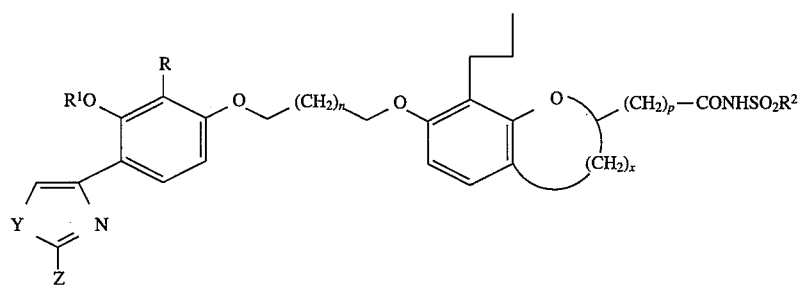

wherein

R represents alkyl having 2 to 4 carbon atoms alkenyl having 3 to 4 carbon atoms, or cyclopropylalkyl wherein the alkyl moiety has 1 to 2 carbon atoms;

$R^1$ represents methyl or ethyl;

$R^2$ represents alkyl having 1 to 3 carbon atoms, aryl or aryl substituted with halogen or alkyl having 1 to 5 carbon atoms;

n is an integer from 1 to 3;

p is an integer from 0 to 4;

x is 0 or 2;

Y represents NH, oxygen, or sulfur; and

Z represents hydrogen, alkyl having 1 to 4 carbon atoms, alkoxy having 1 to 4 carbon atoms, $NH_2$, or $SR^7$ wherein $R^7$ is hydrogen, benzyl or alkyl of 1 to 4 carbon atoms.

These compounds are selective antagonists of leukotriene $B_4$ ($LTB_4$) with little or no antagonism of leukotriene $D_4$ ($LTD_4$) and are useful anti-inflammatory agents for treating inflammatory bowel disease, rheumatoid arthritis, gout, and psoriasis.

More preferred embodiments are compounds of the formula II and the stereoisomers and pharmaceutically acceptable salts thereof

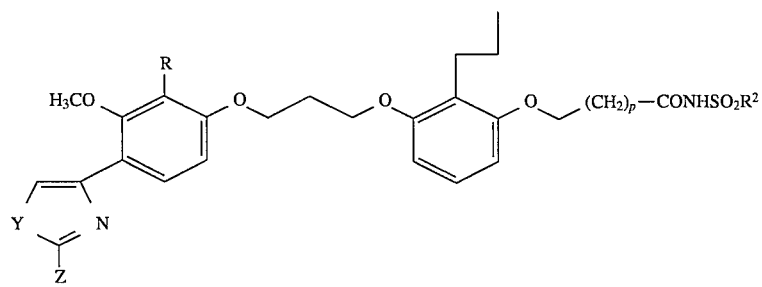

II wherein R represents propyl, 2-propenyl, or cyclopropylmethyl; p is an integer from 0 to 2; Y represents NH, oxygen, or sulfur; and Z represents hydrogen, $NH_2$, alkyl having 1 to 2 carbon atoms, alkoxy having 1 to 2 carbon atoms or $SR^7$ wherein $R^7$ is hydrogen, benzyl or methyl.

Alkyl defined for R, $R^1$, $R^2$, $R^3$, $R^4$, $R^5$, $R^6$ and $R^7$ is straight or branched chain alkyl having the indicated number of carbon atoms.

Pharmaceutically acceptable salts such as ammonium, sodium, potassium, alkaline earth, tetraalkylammonium and the like are encompassed by the invention.

Schemes A, B, C, D and E show general methods for preparing compounds of the invention.

In Scheme A, the imidazoles are prepared using an appropriate methyl ketone to prepare the appropriate α-haloketone which is reacted with 2-benzyl-2-thiopseudourea hydrochloride. The methyl ketone (III) is converted to its silyl enol ether and reacted with a halogenating reagent [i.e., an N-halosuccinimide (NXS)] to give the 4-(2-halo-1-oxoethyl)alkyl ester (IV) which is then reacted with 2-benzyl-2-thiopseudourea hydrochloride to give the 4-[2-(phenylmethyl)thio]-1H-imidazol- 4-yl alkyl ester (V). Hydrolysis of (V) with lithium hydroxide or other suitable base gives the acid (VI). Alternately, reduction of (V) under alkaline conditions gives (VII).

In Scheme B, condensation of ketone (VIII) with an appropriate amide or thioamide gives the appropriately substituted thiazoles or oxazoles (IX) wherein Y=S or O. Hydrolysis of (IX) with lithium hydroxide or another suitable base, gives the acid (X). Alternately when Z in (IX) is —SH, then alkylation of (IX) with an alkyl halide ($AlkX^1$) gives the thioalkyl compound (XI) which can be hydrolyzed to the acid with an appropriate base.

Scheme C shows an alternate synthesis for the substituted thiazoles in which (IV) is reacted with thiocyanate to give the 4-(1-oxo-2-thiocyanatoethyl) compound (XIII) which is then reacted with $Z^-$ where Z may be alkoxy, —SR, —$NH_2$ to give (XIV) followed by reaction with an appropriate base such as lithium hydroxide to give the acid product (XV).

Reaction Scheme D shows how the sulfonimide derivatives that are the subject of the invention herein can be formed from the acids made by Reaction Schemes A, B, and C. In Reaction Scheme C an acid is reacted with the appropriate alkyl sulfonylamine in the presence of EDC (1-(3-dimethylamino)propyl)-3-ethylcarbodiimide), dichloromethane and 4-DMAP (4-dimethylaminopyridine) to form the resultant sulfonimide.

Scheme A
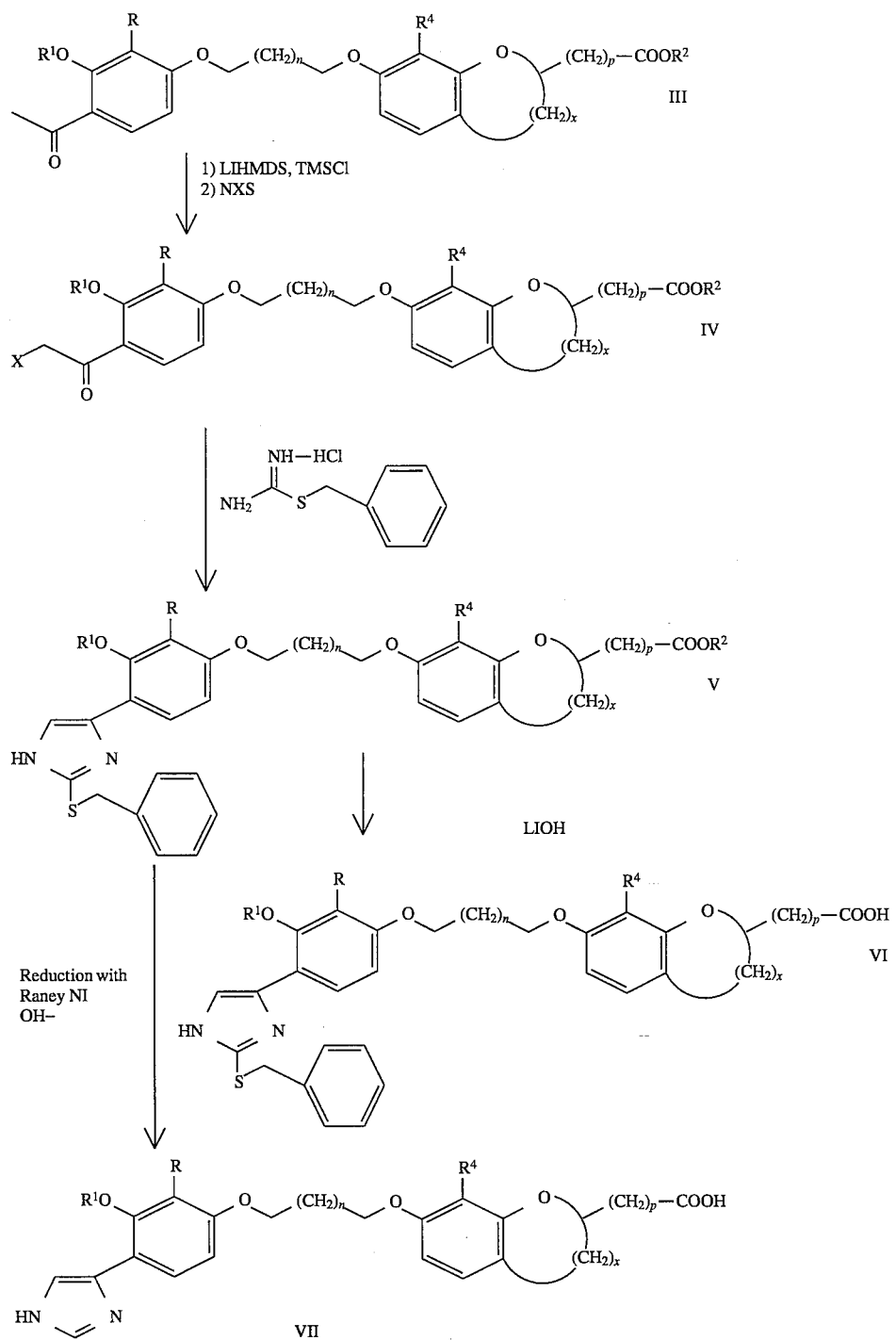
R² = alkyl
Alk = alkyl
X = halogen, preferably Cl
R⁴ = alkyl

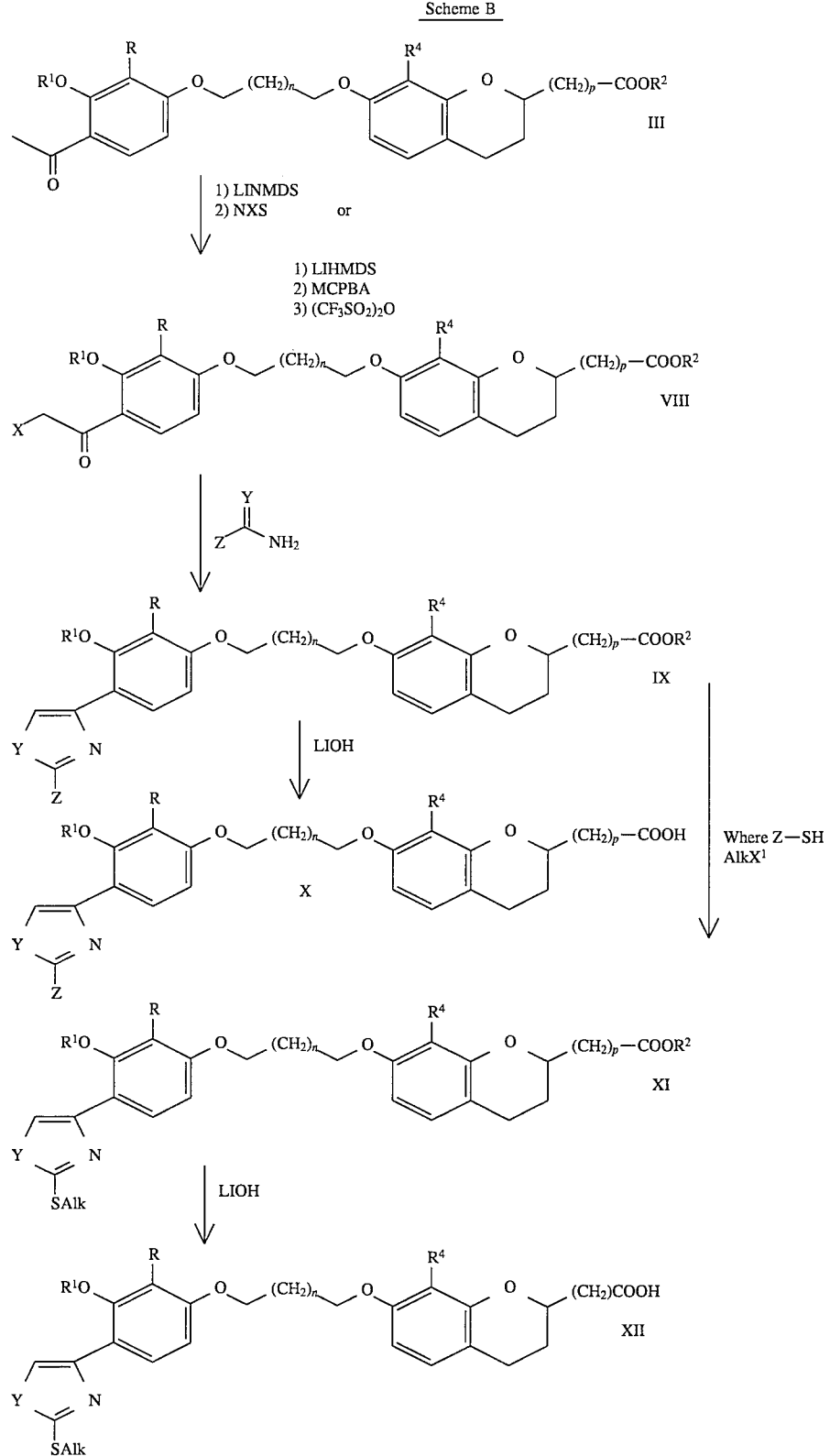

-continued
Scheme B

R² = alkyl
Alk = alkyl
X = halogen or F₃CSO₃
Y = S, O
Z = SH, alkyl, NH₂
X¹ = halogen
R⁴ = alkyl

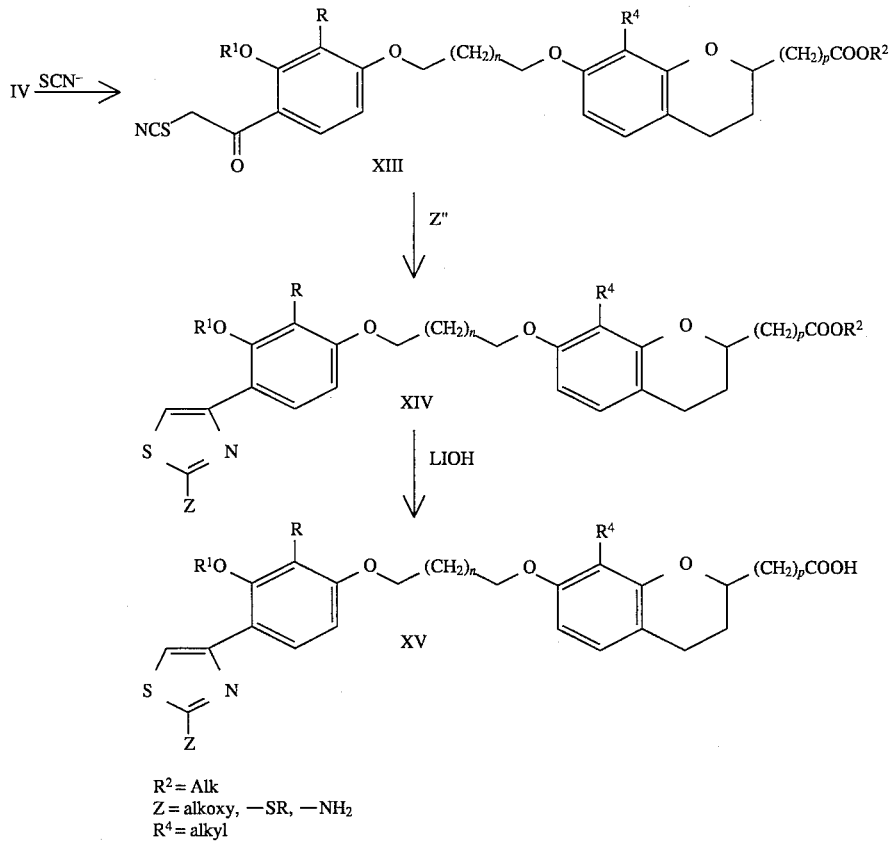

R² = Alk
Z = alkoxy, —SR, —NH₂
R⁴ = alkyl

Scheme D

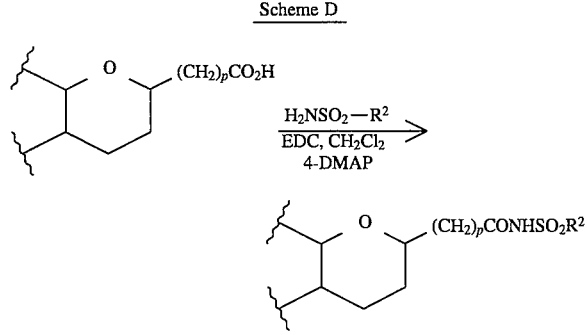

The biological activity of compounds of this invention is indicated by the following tests.

Preparation of Human Neutrophils

Neutrophils were purified from venous blood of normal human donors using standard techniques of dextran sedimentation, centrifugation on Ficoll-paque® (Pharmacia) or Histopaque® sterile solution (Sigma) and hypotonic lysis of erythrocytes (Boyum, A., *Isolation of Leukocytes From Human Blood: Further Observations. Scand. J. Lab. Clin. Invest.*, 21 (Suppl. 97): 31, 1968). The purity of isolated neutrophils was >95%.

LTB₄ Receptor Binding Assay

Neutrophils (4- 6×10⁶) in 1 ml Hanks' balanced salt solution (HBSS) containing 10 mM HEPES buffer, pH 7.4 and 20 mM nordihydroguaiaretic acid were incubated with $0.6 \times 10^{-9}$M ($^3$H) LTB₄ in the presence or absence of test compounds. The incubation was carried out at 0° C. for 45 minutes and terminated by adding 5 ml of ice-cold HBSS followed by rapid filtration of the incubation mixture under vacuum through GF/C glass fiber filters. The filters were further washed with 10 ml HBSS and radioactivity was determined. Specific binding was defined as the difference between total binding and nonspecific binding which was not displaced by $10^{-7}$M unlabeled $LTB_4$. All data refer to specific binding.

Modified Boyden Chamber Chemotaxis

Human neutrophils were isolated from citrated peripheral blood using standard techniques of dextran sedimentation, followed by centrifugation on Histopaque® sterile solution (Sigma) or Ficoll-paque® (Pharmacia) and hypotonic lysis of erythrocytes. A final cell suspension of $3.4 \times 10^6$ neutrophils/ml of HEPES-buffered Hanks' balanced salt solution (HBSS, pH 7.3) was added to the upper well (0.8 ml) of a modified Boyden chamber (blind well). The lower well (0.2 ml), separated by a polycarbonate membrane (Nucleopore Corp.), contained HBSS or $3 \times 10^{-8}$M $LTB_4$ in the presence or absence of test compound. Following a 40–90 minute incubation at 37° C. in 5% $CO_2$-95% air, cells from the lower well were lysed and nuclei counted in a Model S-Plus-IV Coulter Counter. The number of neutrophils migrating into the lower chamber in the absence of chemoattractant was subtracted from the number of cells migrating in the presence of a chemoattractant. Inhibition of chemotaxis by test compounds was expressed as percent inhibition relative to uninhibited control.

Results for representative compounds of the invention are shown in Table 1.

Data are expressed as potency relative to the compound of Example 1(b), 7-[3, (4-acetyl-3-methoxy-2-propylphenoxy)propoxy]-3,4-dihydro-8-propyl-2H-1-benzopyran-2-carboxylic acid, which is disclosed in U.S. Pat. No. 4,889,871.

TABLE 1

| Values for $LTB_4$ Antagonists[1] | | |
|---|---|---|
| Compound | $LTB_4$ Receptor Binding | Chemotaxis $LTB_4$ |
| Example 1(b) | 42 | 1050 |
| Example 9 | 5.5 | 53 |
| Example 15 | 4.3 | 66 |

[1]Values refer to $IC_{50}$ values (nM) for the compounds.

The compounds of this invention can be administered in a number of dosage forms. A preferred method of delivery would be oral or in such a manner so as to localize the action of the antagonist. In an inflammatory condition such as rheumatoid arthritis the compounds could be injected directly into the affected joint. The compounds could also be administered in oral unit dosage forms such as tablets, capsules, pills, powders or granules. They may be introduced intraperitoneally, subcutaneously, or intramuscularly using forms known to the pharmaceutical art. Topical application in the form of salves and ointments are useful for treating psoriasis. Regardless of the route of administration selected, the compounds are formulated into pharmaceutically acceptable dosage forms by conventional methods known to the pharmaceutical art.

The compounds may be administered in a number of dosage forms, for example, such oral dosage forms as tablets, capsules, pills, powders, or granules. They may also be administered intravascularly, intraperitoneally, subcutaneously, topically or intramuscularly using forms known to the pharmaceutical art.

In general, a unit dosage of a compound of the invention would contain from about 50 mg to about 500 mg of the active ingredient with from about 70 mg to about 300 mg preferred.

An effective but non-toxic quantity of the compound is employed in treatment. The dosage regimen for antagonism of $LTB_4$ by the compounds of this invention is selected in accordance with a variety of factors including the type, age, weight, sex, and medical condition of the mammal, the particular disease and its severity, the route of administration and the particular compound employed. An ordinarily skilled physician or Veterinarian will readily determine and prescribe the effective amount of the compound to prevent or arrest the progress of the condition. In so proceeding, the physician or veterinarian could employ or use relatively low dosages at first, subsequently increasing the dose until a maximum response is obtained. Generally, a dosage range of 1 to 25 mg/kg of body weight is administered to patients in need of treatment for inflammatory conditions.

The following examples illustrate the preparation of compounds of this invention from known starting materials. The invention, which is set forth in the foregoing disclosure, is not to be construed or limited either in spirit or in scope by these examples. Those skilled in the art will readily understand that known variations of the conditions and processes of the following preparative procedures can be used to prepare these compounds. All temperatures are degrees Celsius unless otherwise noted.

U.S. Pat. No. 4,665,203 issued May 12, 1987 incorporated herein by reference, U.S. Pat. No. 4,889,871, incorporated herein by reference, and European Application EP 0292977 published Nov. 30, 1988 disclose methods for making some of the intermediates used in making compounds of the present invention. U.S. Pat. No. 5,073,562 issued Dec. 17, 1991 is incorporated herein by this reference. U.S. Pat. No. 5,073,562 discloses the carboxylic acid compounds and methods for their synthesis.

For the chemical structures drawn herein, wherein a bond is drawn without a functional group at the end of the bond, it is intended to mean that the terminal group on such bond is a methyl group.

EXAMPLE 1

(a) Methyl 7-[3-(4-acetyl-3-methoxy-2-propylphenoxy)propoxy]-3,4-dihydro-8-propyl-2H-1-benzopyran-2-carboxylate

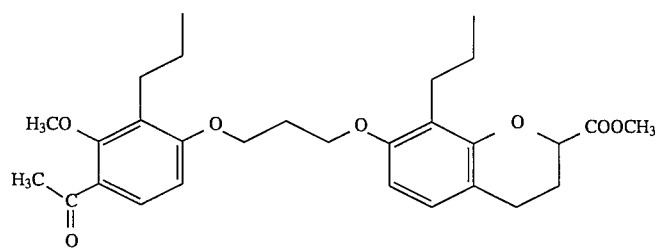

1a

Methyl 7-[3-(4-acetyl-3-hydroxy-2-propyl-phenoxy)propoxy]-3,4-dihydro-8-propyl-2H-1-benzopyran-2-carboxylate (493 mg) was added to 25 ml of acetone containing 276 mg of anhydrous potassium carbonate and 282 mg of methyl iodide. The mixture was refluxed for about 24 hours and water was added and the mixture was then extracted with ethyl acetate. The extract was dried, the solvent removed under vacuum, and the residual oil was chromatographed over silica gel with a 40/60 mixture of ethyl acetate/hexane to provide pure methyl ether, methyl 7-[3-(4-acetyl-3-methoxy-2-propylphenoxy)propoxy]-3,4-dihydro-8-propyl-2H-1-benzopyran-2-carboxylate.

EXAMPLE 1(b)

7-[3-(4-acetyl-3-methoxy-2-propylphenoxy)propoxy]-3,4-dihydro-8-propyl-2H-1-benzopyran-2-carboxylic acid

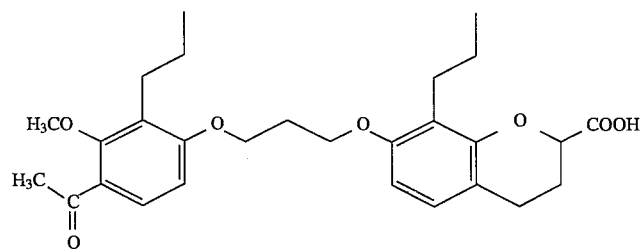

(b) The methyl ether (1a) (340 mg) was dissolved in methanol (5 ml) containing lithium hydroxide (0.7 ml of a 2N LiOH solution in water). The mixture was stirred at room temperature overnight and the solvent removed in vacuo. The residue was partitioned between ethyl acetate and 2N HCl and the organic layer separated and washed with brine. Evaporation of the volatiles in vacuo afforded crude acid of Formula III. This material was purified by silica gel chromatography using ethyl acetate/hexane/acetic acid (40:60:0.5) as eluant. The pure product was recrystallized from ethyl acetate/hexane to afford 200 mg of product, 7-[3-(4-acetyl-3-methoxy-2-propylphenoxy)propoxy]-3,4-dihydro-8-propyl-2H-1-benzopyran-2-carboxylic acid, m.p. 65°–68° C.

Microanalysis: Found: C 69.22, H 7.53. Theory: C 69.40, H 7.49. The NMR (CDCl$_3$) shows a —OCH$_3$ at δ3.75.

EXAMPLE 2

Methyl sulfonimide of 3,4-Dihydro-7-[3-[3-methoxy-4-(4-oxazolyl)-2-propylphenoxy]propoxy]-8-propyl-2H-1-benzopyran-2-carboxylic acid

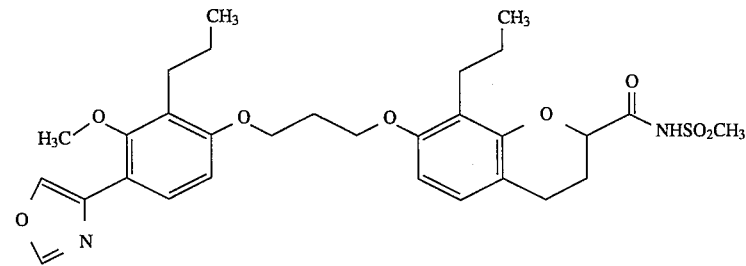

3,4-Dihydro-7-[3-[3-methoxy-4-(4-oxazolyl)-2-propylphenoxy]propoxy]-8-propyl-2H-1-benzopyran-2-carboxylic acid was prepared in the manner described in U.S. Pat. No. 5,073,562. A sulfonimide of the above formula is prepared following the procedure of Scheme D using methyl sulfonylamine.

EXAMPLE 3

Methyl sulfonimide of 3,4-Dihydro-7-[3-[3-methoxy-4-[2-[(phenylmethyl)thio]-1H-imidazol-4-yl]-2-propylphenoxy]propoxy]-8-propyl-2H-1-benzopyran-2-carboxylic acid

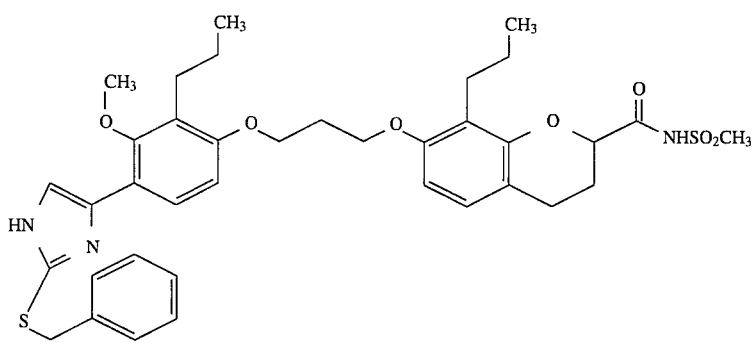

3,4-Dihydro-7-[3-[3-methoxy-4-[2-[(phenylmethyl)thio]-1H-imidazol-4-yl]-2-propylphenoxy]propoxy]-8-propyl-2H-1-benzopyran-2-carboxylic acid was prepared in the manner described in U.S. Pat. No. 5,073,562. A sulfonimide of the above formula is prepared following the procedure of Scheme D using methyl sulfonylamine.

EXAMPLE 4

Methyl sulfonimide of 3,4-Dihydro-7-[3-[4-(1H-imidazol-4-yl)-3-methoxy-2-propylphenoxy]propoxy]-8-propyl-2H-1-benzopyran-2-carboxylic acid

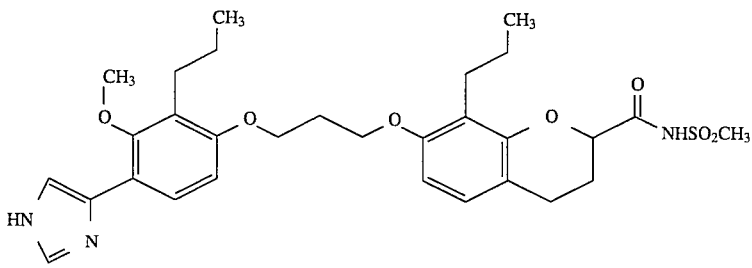

3,4-Dihydro-7-[3-[4-(1H-imidazol-4-yl)-3-methoxy-2-propylphenoxy]propoxy]-8-propyl-2H-1-benzopyran-2-carboxylic acid was prepared in the manner described in U.S. Pat. No. 5,073,562. A sulfonimide of the above formula is prepared following the procedure of Scheme D using methyl sulfonylamine.

EXAMPLE 5

Methyl sulfonimide of 7-[3-[4-(2-amino-4-thiazolyl)-3-methoxy-2-propylphenoxy]propoxy]3,4-dihydro-8-propyl-2H-1-benzopyran-2-carboxylic acid

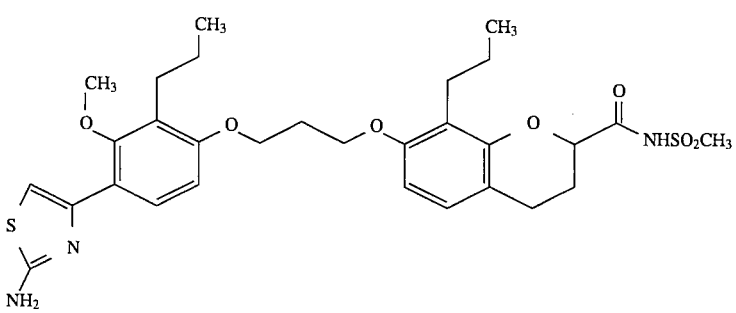

7-[3-[4-(2-amino-4-thiazolyl)3-methoxy-2-propylphenoxy]propoxy]3,4-dihydro-8-propyl-2H-1-benzopyran-2-carboxylic acid was prepared in the manner described in U.S. Pat. No. 5,073,562. A sulfonimide of the above formula is prepared following the procedure of Scheme D using methyl sulfonylamine.

EXAMPLE 6 p-chlorophenyl sulfonimide of 3,4-dihydro-7-[3-[3-methoxy-2-propyl-4-(4-thiazolyl)phenoxy]propoxy]-8-propyl-2H-1-benzopyran-2-carboxylic acid

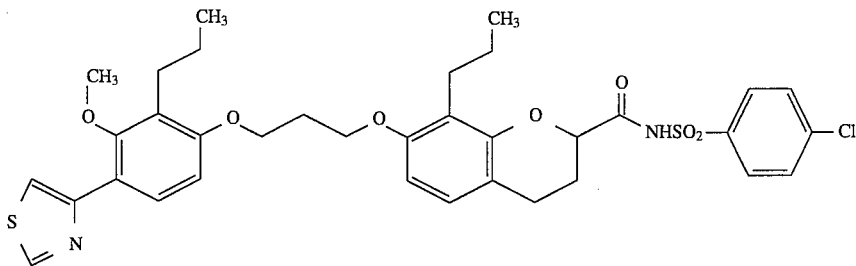

3,4-dihydro-7-[3-[3-methoxy-2-propyl-4-(4-thiazolyl)phenoxy]-propoxy]-8-propyl-2H-1-benzopyran-2-carboxylic acid was prepared in the manner described in U.S. Pat. No. 5,073,562. A sulfonimide of the above formula is prepared following the procedure of Scheme D using p-chlorophenyl sulfonylamine.

EXAMPLE 7 p-chlorophenyl sulfonimide of 3,4-dihydro-7-[3-[3-methoxy-4-(2-methyl-4-oxazolyl)-2-propylphenoxy]propoxy]-8-propyl-2H-1-benzopyran-2-carboxylic acid

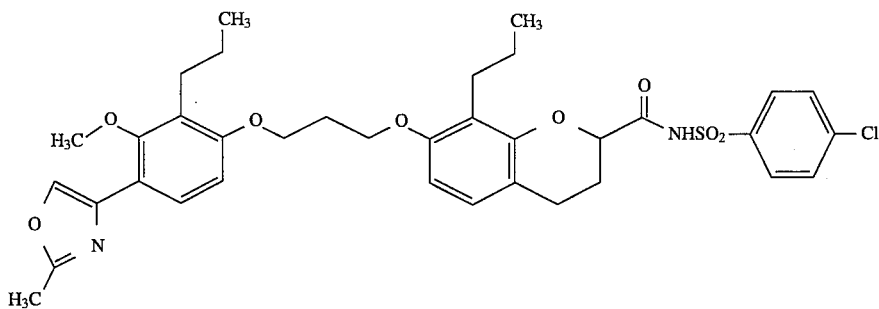

3,4-dihydro-7-[3-[3-methoxy-4-(2-methyl-4-oxazolyl)-2-propylphenoxy]propoxy]-8-propyl-2H-1-benzopyran-2-carboxylic acid was prepared in the manner described in U.S. Pat. No. 5,073,562. A sulfonimide of the above formula is prepared following the procedure of Scheme D using p-chlorophenyl sulfonylamine.

EXAMPLE 8 toluyl sulfonimide of 3,4-dihydro-7-[3-[3-methoxy-2-(2-propenyl)-4-(4-thiazolyl)-phenoxy]propoxy]-8-propyl-2H-1-benzopyran-2-carboxylic acid

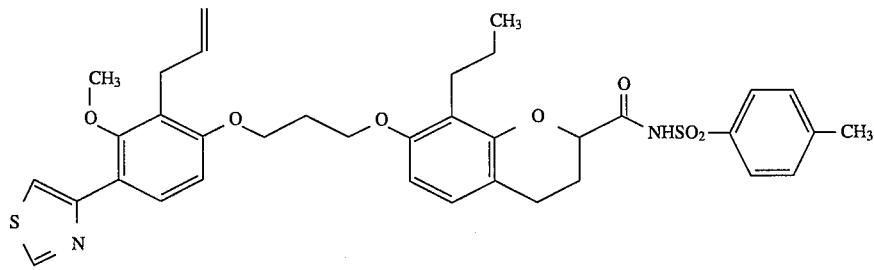

3,4-dihydro-7-[3-[3-methoxy-2-(2-propenyl)-4-(4-thiazolyl)-phenoxy]propoxy]-8-propyl-2H-1-benzopyran-2-carboxylic acid was prepared in the manner described in U.S. Pat. No. 5,073,562. A sulfonimide of the above formula is prepared following the procedure of Scheme D using p-tolyl sulfonylamine.

EXAMPLE 9

Benzo sulfonimide of 7-[3-[2-(Cyclopropylmethyl)-3-methoxy-4-(4-thiazolyl)phenoxy]propoxy]-3,4-dihydro-8-propyl-2H-1-benzopyran-2-carboxylic acid

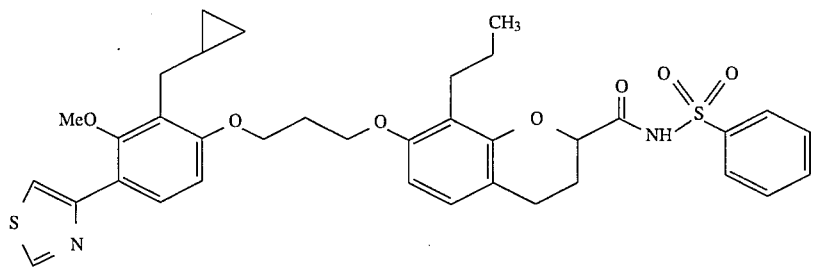

7-[3-[2-(Cyclopropylmethyl)-3-methoxy-4-(4-thiazolyl)phenoxy]propoxy]-3,4-dihydro-8-propyl-2H-1-benzopyran-2-carboxylic acid was prepared in the manner described in U.S. Pat. No. 5,073,562. A sulfonimide of the above formula is prepared following the procedure of Scheme D. In a reaction flask was added 51 mg (95 μmol) of the acid, 15 mg (95 μmol) of phenyl sulfonyl amide, 14 mg (115 μmol) of DMAP, 19 mg (96 μmol) EDC, 5 ml of dichloromethane. The reaction mixture was stirred with 4 Angstrom molecular sieves and held at room temperature for 24 hours. The reaction mixture was poured into a solution of ethyl acetate and 0.5 normal hydrochloric acid and extracted with ethyl acetate. The ethyl acetate was dried over $Na_2SO_4$ and concentrated under vacuum. Following flash chromatography using a gradient of 3:1 to 1:1 hexane/ethyl acetate yielded 29 mg (43 μmol) of the above identified phenyl sulfonimide.

EXAMPLE 10

Toluyl sulfonimide of 3,4-Dihydro-7-[3-[3-methoxy-4-(2-methoxy-4-thiazolyl)-2-propylphenoxy]propoxy]-8-propyl-2H-1-benzopyran-2-carboxylic acid

EXAMPLE 11

Methyl sulfonimide of 3,4-Dihydro-7-[3-[4-(2,3-dihydro-2-thioxo-4-thiazolyl)-3-methoxy-2-propylphenoxy]propoxy]-8-propyl-2H-1-benzopyran-2-carboxylic acid

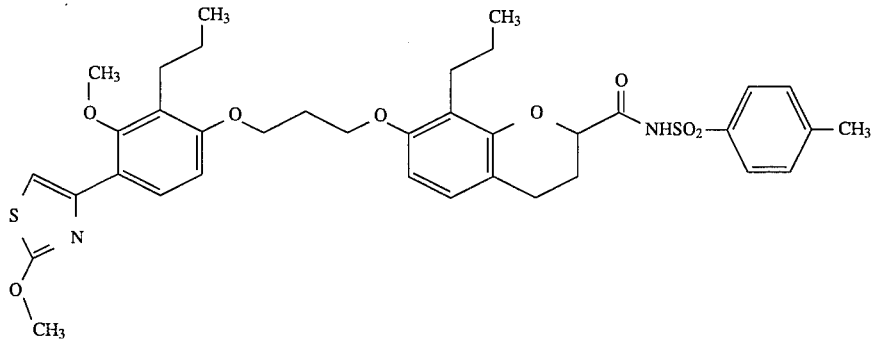

3,4-Dihydro-7-[3-[3-methoxy-4-(2-methoxy-4-thiazolyl)-2-propylphenoxy]propoxy]-8-propyl-2H-1-benzopyran-2-carboxylic acid was prepared in the manner described in U.S. Pat. No. 5,073,562. A sulfonimide of the above formula is prepared following the procedure of Scheme D using p-tolyl sulfonylamine.

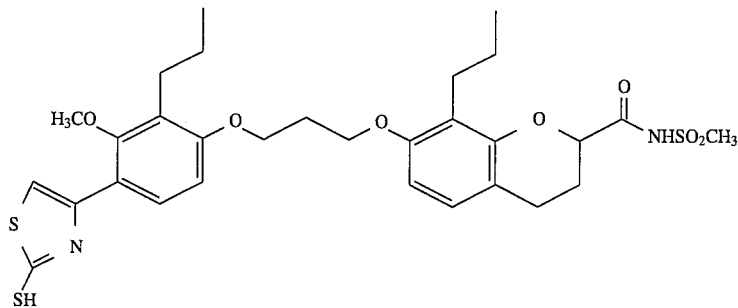

3,4-Dihydro-7-[3-[4-(2,3-dihydro-2-thioxo-4-thiazolyl)-3-methoxy-2-propylphenoxy]propoxy]-8-propyl-2H-1-benzopyran-2-carboxylic acid was prepared in the manner described in U.S. Pat. No. 5,073,562. A sulfonimide of the above formula is prepared following the procedure of Scheme D using methyl sulfonylamine.

EXAMPLE 12

Methyl sulfonimide of 3,4-Dihydro-7-[3-[3-methoxy-4-[2-(methylthio)-4-thiazolyl]-2-propylphenoxy]propoxy]-8-propyl-2H-1-benzopyran-2-carboxylic acid

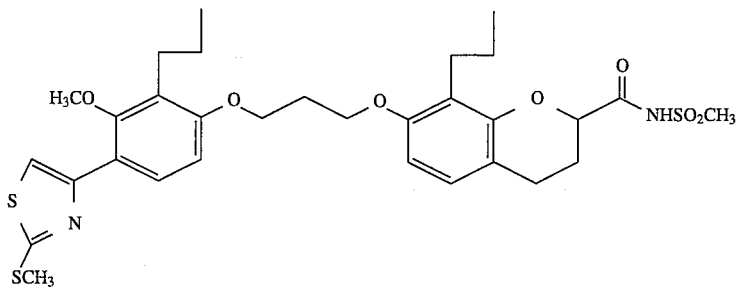

3,4-Dihydro-7-[3-[3-methoxy-4-[2-(methylthio)-4-thiazolyl]-2-propylphenoxy]propoxy]-8-propyl-2H-1-benzopyran-2-carboxylic acid was prepared in the manner described in U.S. Pat. No. 5,073,562. A sulfonimide of the above formula is prepared following the procedure of Scheme D using methyl sulfonylamine.

EXAMPLE 13

Methyl sulfonimide of 3,4-Dihydro-7-[3-[3-methoxy-4-[2-[(phenylmethyl)thio]-4-thiazolyl]-2-propylphenoxy]propoxy]-8-propyl-2H-1-benzopyran-2-carboxylic acid

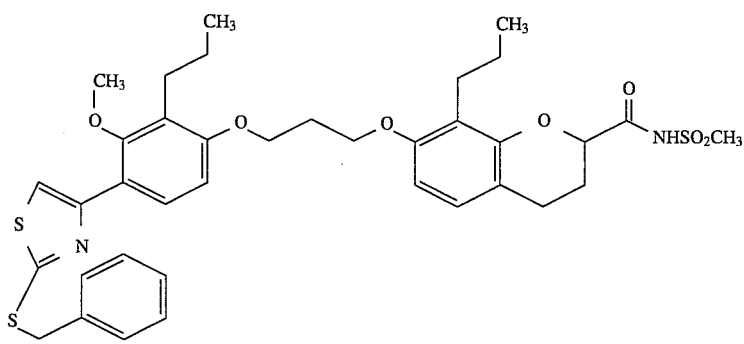

3,4-Dihydro-7-[3-[3-methoxy-4-[2-[(phenylmethyl)thio]-4-thiazolyl]-2-propylphenoxy]propoxy]-8-propyl-2H-1-benzopyran-2-carboxylic acid was prepared in the lo manner described in U.S. Pat. No. 5,073,562. A sulfonimide of the above formula is prepared following the procedure of Scheme D using methyl sulfonylamine.

EXAMPLE 14

Methyl sulfonimide of 3,4-Dihydro-7-[3-[3-methoxy-2-propyl-4-(4-thiazolyl)phenoxy]propoxy]-8-propyl-2H-1-benzopyran-2-propionic acid

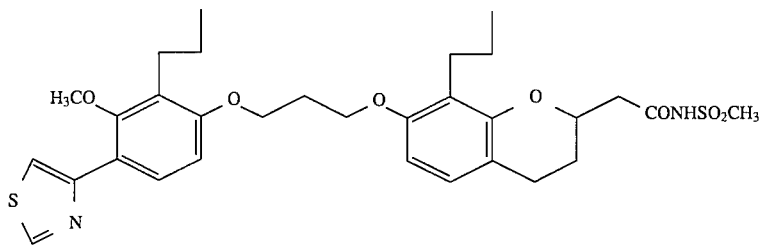

3,4-Dihydro-7-[3-[3-methoxy-2-propyl-4-(4-thiazolyl)phenoxy]propoxy]-8-propyl-2H-1-benzopyran-2-propionic acid was prepared in the manner described in U.S. Pat. No. 5,073,562. A sulfonimide of the above formula is prepared following the procedure of Scheme D using methyl sulfonylamine.

EXAMPLE 15

Benzo sulfonimide of 3,4-Dihydro-7-[3-[3-methoxy-2-cycloproplymethyl-4-(4-thiazolyl)phenoxy]propoxy]-8-propyl-2H-1-benzopyran-2-propionic acid

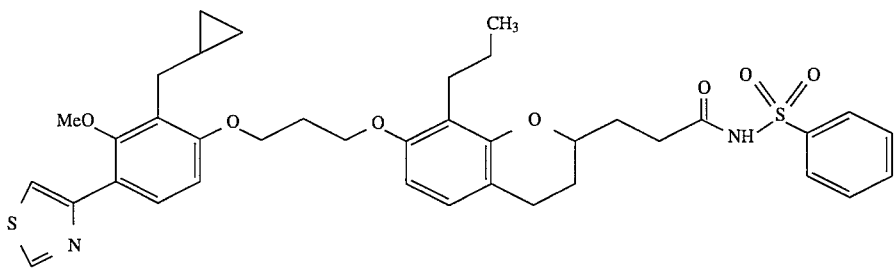

In a reaction vessel was added 34 mg (60 μmol) of the following acid synthesized as described in U.S. Pat. No. 5,073,562:

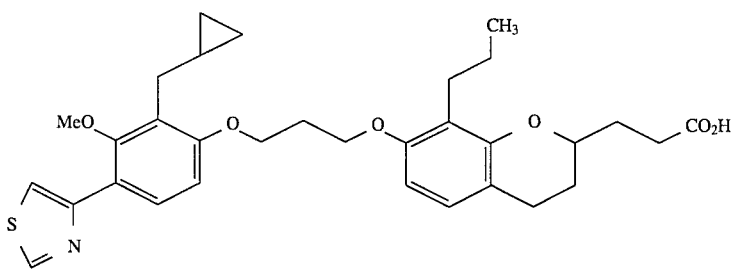

10 mg (64 μmol) of phenyl sulfonylamine, 8 mg (73 μmol) of DMAP, 5 ml of dichloromethane and the reaction mixture was stirred with 4 Angstrom molecular sieves. To the mixture was added 12 mg (61 μmol) of EDC and the reaction mixture was held at room temperature for 24 hours. The mixture was poured into a solution of ethyl acetate and a 0.5 normal hydrochloric acid and extracted with ethyl acetate. The ethyl acetate was dried over $Na_2SO_4$ and concentrated under vacuum. Flash chromatography using a gradient of 5:1 to 1:1 hexane/ethyl acetate mixture yielded 24 mg (34 μmol) of the above phenyl sulfonimide.

What is claimed is:

1. A compound of the formula:

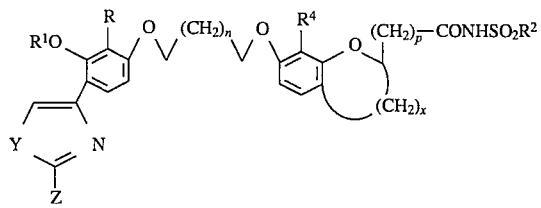

wherein

R represents alkyl having 2 to 6 carbon atoms, alkenyl having 2 to 6 carbon atoms, alkynyl having 2 to 6 carbon atoms, or $-(CH_2)_m-R^3$ wherein $R^3$ represents cycloalkyl of 3 to 5 carbons atoms and m is 1 or 2;

$R^1$ represents alkyl having 1 to 4 carbon atoms;

$R^2$ represents alkyl having 1 to 5 carbon atoms, phenyl or phenyl substituted with halogen or alkyl having 1 to 5 carbon atoms;

$R^4$ represents alkyl having 1 to 6 carbon atoms;

n is an integer from 1 to 5;

p is an integer from 0 to 6;

x is 0 or 2;

Y represents NH, oxygen or sulfur; and

Z represents hydrogen, alkyl having 1 to 4 carbon atoms, alkoxy having 1 to 4 carbon atoms, NR⁶R⁵
wherein
R⁶ and R⁵ are independently hydrogen or alkyl having 1 to 4 carbon atoms, or SR⁷ wherein R⁷ is, hydrogen, benzyl or alkyl having 1 to 4 carbon atoms; and the stereoisomers and pharmaceutically acceptable salts thereof.

2. A compound according to claim 1 of the formula

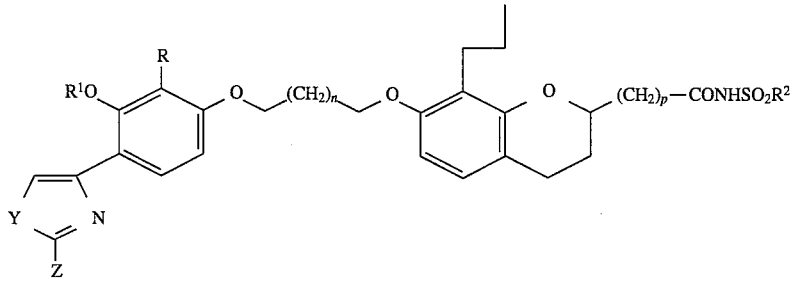

wherein
R represents alkyl having 2 to 4 carbon atoms, alkenyl having 3 to 4 carbon atoms, or cyclopropylalkyl wherein the alkyl moiety has 1 to 2 carbon atoms;
R¹ represents methyl or ethyl;
R² represents alkyl having 1 to 3 carbon atoms, phenyl or phenyl substituted with halogen or alkyl having 1 to 5 carbon atoms;
n is an integer from 1 to 3;
p is an integer from 0 to 4;
Y represents NH, oxygen, or sulfur; and
Z represents hydrogen, alkyl having 1 to 4 carbon atoms, alkoxy having 1 to 4 carbon atoms, NH₂ or SR⁷ wherein R⁷ is, hydrogen, benzyl, or alkyl having 1 to 4 carbon atoms; and the stereoisomers and pharmaceutically acceptable salts thereof.

3. A compound according to claim 1 of the formula

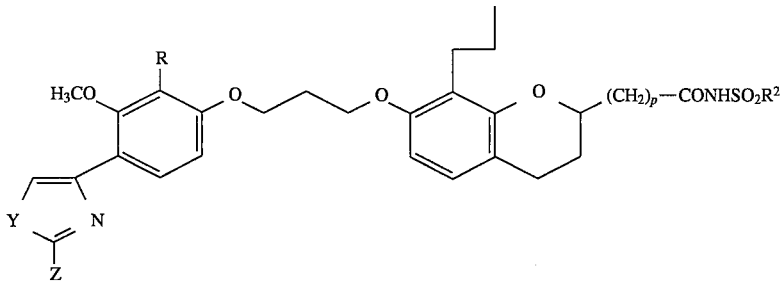

wherein
R represents propyl, 2-propenyl, or cyclopropylmethyl;
R² is phenyl;
p is an integer from 0 to 2;

Y represents NH, oxygen, or sulfur; and
Z represents hydrogen, NH₂, alkyl having 1 to 2 carbon atoms, alkoxy having 1 to 2 carbon atoms, or SR⁷ wherein R⁷ is hydrogen, benzyl or methyl; and the stereoisomers and pharmaceutically acceptable salts thereof.

4. A compound as recited in claim 3 wherein Y is sulfur.

5. A compound as recited in claim 4 wherein Z is hydrogen.

6. A pharmaceutical composition comprising a therapeutically effective amount of a compound of claim 1 and a pharmaceutically acceptable carrier.

7. A method of treating leukotriene B₄ mediated conditions comprising administering to a mammal in need of such treatment a therapeutically effective amount of a compound of claim 1.

8. A method according to claim 7 wherein the leukotriene B₄ mediated condition is rheumatoid arthritis.

9. A method according to claim 7 wherein the leukotriene B₄ mediated condition is psoriasis.

10. A method according to claim 7 wherein the leukotriene B₄ mediated condition is inflammatory bowel disease.

11. A method according to claim 7 wherein the leukotriene B₄ mediated condition is gout.

12. A method according to claim 7 wherein the leukotriene B₄ mediated condition is asthma.

13. A method according to claim 7 wherein the leukotriene B₄ mediated condition is multiple sclerosis.

* * * * *

UNITED STATES PATENT AND TRADEMARK OFFICE
CERTIFICATE OF CORRECTION

PATENT NO. : 5,578,619

DATED : November 26, 1996

INVENTOR(S) : STEVAN W. DJURIC, ET AL.

It is certified that error appears in the above-identified patent and that said Letters Patent is hereby corrected as shown below:

ON TITLE PAGE AT [76] INVENTORS

"[76]" should read --[75]--.

ON TITLE PAGE AFTER [76] INVENTORS

Insert -- [73] Assignee: G.D. Searle & Co., Chicago, Ill.--.

ON TITLE PAGE AT [56], REFERENCES CITED

Under U.S. Patent Documents, insert
--5,380,740  01/10/96 Djuric, et al.  514/382--.

After U.S. Patent Documents, insert
--FOREIGN PATENT DOCUMENTS
WO91/17989  11/28/91  PCT
0 139 809   05/08/85  European
0 292 977   11/30/88  European--.

At Other Publications

Under K. Shindo, et al., "bllod" should read --blood--.
Under R. Barr et al., "(1994)" should read --(1984)--.
Under T. Schaar, "Schaar" should read --Schaaf--.

Insert after Fretland, D.J. ... Encephalomyelitis.
--Fretland, D.J. et al. *Inflammation*, 17, 353-360 (1993). "Leukotriene $B_4$-induced granulocyte trafficking in guinea pig dermis: Effect of second-generation leukotriene $B_4$ receptor antagonists, SC-50605 and SC-51146".--.

UNITED STATES PATENT AND TRADEMARK OFFICE
CERTIFICATE OF CORRECTION

PATENT NO.  : 5,578,619

DATED       : November 26, 1996

INVENTOR(S) : STEVAN W. DJURIC, ET AL.

Page 2 of 3

It is certified that error appears in the above-identified patent and that said Letters Patent is hereby corrected as shown below:

Insert after V. Matassa ... 1990),

--Penning, T.D., et al., *J. Med. Chem.* $\underline{38}$, 858-868 (1995) "Second-Generation Leukotriene $B_4$ Receptor Antagonists Related to SC-41930: Heterocyclic Replacement of the Methyl Ketone Pharmacophore".

Penning, T.D., et al., *Agents and Actions*, $\underline{38}$, pp. C11-C13, (1993). "The design and synthesis of second generation leukotriene $B_4$ ($LTB_4$) receptor antagonists related to SC-41930.--

COLUMN 12

Line 19, "Veterinarian" should read --veterinarian--.

COLUMN 22

Line 17, "lo" should be deleted.

UNITED STATES PATENT AND TRADEMARK OFFICE
CERTIFICATE OF CORRECTION

PATENT NO. : 5,578,619

DATED : November 26, 1996

INVENTOR(S) : STEVAN W. DJURIC, ET AL.

It is certified that error appears in the above-identified patent and that said Letters Patent is hereby corrected as shown below:

<u>COLUMN 24</u>

Line 55, "carbons" should read --carbon--.

Signed and Sealed this

Twentieth Day of February, 2001

*Attest:*

NICHOLAS P. GODICI

*Attesting Officer*   Acting Director of the United States Patent and Trademark Office